United States Patent [19]

Barberet et al.

[11] Patent Number: Plant 6,211

[45] Date of Patent: Jun. 21, 1988

[54] CARNATION NAMED LONBROSIO

[75] Inventors: Nicole Barberet; Yves Ducloux, both of Antibes, France

[73] Assignee: Laboratoire de Physiologie Vegetale de la Londe, La Londe, France

[21] Appl. No.: 872,243

[22] Filed: Jun. 9, 1986

[51] Int. Cl.[4] ..... A01H 5/00

[52] U.S. Cl. ..... Plt./73

[58] Field of Search ..... Plt./70–73

*Primary Examiner*—James R. Feyrer

*Attorney, Agent, or Firm*—Charles W. Rummler; W. Dennis Drehkoff

[57] ABSTRACT

A new carnation cultivar having relatively large, bright red blooms which are produced profusely on relatively long, strong, upright stems, blooming recurrently in spring, midseason and fall on a plant having a vigorous, upright growth habit and moderately abundant foliage.

1 Drawing Sheet

BACKGROUND OF THE NEW PLANT

This new carnation cultivar originated as a seedling resulting from our crossing of selected varieties of stock plants maintained by us at La Londe, Les Maures, France, for breeding purposes, the crossing having been made with the object of developing new and unusual varieties of good commercial quality and having a strong resistance to *Fusarium oxysporum.* We selected this seedling for propagation because of the brilliant red color of its flowers and its apparently vigorous growth habit and this was done by means of cuttings with very satisfactory results. For that reason, this new plant was propagated under our direction through several successive generations by means of cuttings and in vitro propagation procedures and this work, done at La Londe under our direction, demonstrated that this new plant would maintain its distinctive characteristics from generation to generation and that these characteristics appeared to be firmly fixed.

DESCRIPTION OF THE DRAWING

Our new carnation cultivar is illustrated by the accompanying photographic drawing which shows, in full color, several blossoms and a bud with stems and foliage, the colors shown being as nearly true as it is reasonably possible to obtain by conventional photographic procedures.

DESCRIPTION OF THE NEW PLANT

The following is a detailed description of our new carnation cultivar based upon observations made in the spring of the current year at La Londe, the color designations being according to The R.H.S. Colour Chart published by The Royal Horticultural Society of London, England.

THE PLANT

Origin: Seedling.

Parentage:

*Seed parent.*—Plant No. 75 MR 16.

*Pollen parent.*—Plant No. 8391 P. Both of these plants are maintained in our field of plants maintained for breeding purposes and the characteristics of each are recorded in our breeding records under their respective identification numbers.

Classification:

*Botanic.*—*Dianthus caryophyllus.*

*Commercial.*—Standard carnation.

Form: Erect bush comprising at least four stems emitted near the ground.

Height: Approximately 95 cm., in average at 8 months.

Growth: Vigorous, strong and upright. Rigid in character.

Branching: This plant has a few branches.

Foliage:

*Quantity.*—Moderately abundant.

*Number of leaves.*—More than 120.

*Size of leaf* (at the 7th node).—About 16 cm. long and about 1 cm. wide, in average.

*Leaf shape.*—Generally linear and with rolled margins.

*Texture.*—Leathery.

*Color.*—Upper and under sides — Greyed Green, 189A+B.

*Leaflets.*—None.

*Ribs and veins.*—Hardly noticeable.

*Rachis.*—Hardly noticeable.

THE BUD

Size: Large.

*Diameter.*—About 2.6 cm., in average.

*Length.*—About 3 cm., in average.

Form: Ovoid.

Rate of opening: Normal.

Color of petals:

*When sepals first divide and petals begin to unfurl-*.—Bright red as in full bloom.

Sepals:

*Shape.*—The sepals are hooded over the bud before dividing and stand up as the flower petals unfurl. The sepals are joined together at the lower part and are sharp pointed at the apex.

*Number.*—5 or 6 (usually 6).

*Color.*—Inside, 145D+181C at the extremity. Outside, 138C+144D.

Calyx:

*Shape.*—Funnel-shaped.

*Size.*—Large, broad and medium long.

*Aspect.*—Smooth.

*Splitting.*—Sometimes the calyx splits.

Flower stem:

*Length.*—About 65 cm.

*Character.*—Rigid and erect.

*Color.*—Dark Green, 189A and B.

THE FLOWER

Blooming habit: Recurrent, blooming profusely in the spring, midseason and fall, with a tendency to give less blooms in fall.

Size of bloom: Large.

*Diameter.*—About 7.8 cm., in average.

*Depth.*—About 5.5 cm., in average.

Borne: Singly on rigid, erect stems.

Shape: High centered when bloom first opens and becoming rounded when the bloom matures.

Petalage:

*Number of petals.*—76 to 84, averaging about 78.

*Arrangement.*—Imbricated.

*Form.*—Fan-shaped with rounded edges and serrated apex.

*Texture.*—Soft.

*Appearance.*—Shiny.

*Color.*—Outer petal: Top side: Body: 45B with greenish base. Reverse side: 45D. Inside petals: Body: 45B, greenish at base. Reverse side: 45D.

Petaloids: About 2 to 9 in number and somewhat smaller than petals.

*Color.*—The same as the petals.

Flower stem:

*Length.*—About 65 cm.

*Color.*—Grey Green, 189A to 189B.

*Character.*—Strong and upright.

Fragrance: Perceptible.

Persistence: The petals hang on and dry.

Lasting quality:

*As cut flower.*—At least ten days in vase keeping.

REPRODUCTIVE ORGANS

Stamens:

*Anthers.*—Number: 6 to 10 arranged around the ovary. Size: Less than 4 mm. Color: Whitish.

*Filaments.*—Color: Whitish.

Pistils:

*Number.*—4 to 6.

Styles:

*Color.*—Red.

Stigmas:

*Color.*—Red.

Character of ovaries: The ovaries are ribbed.

This new carnation cultivar most resembles "Lontarion" (U.S. Plant Pat. No. 5,435) and "Londanelle" (U.S. Plant Pat. No. 5,516). However, this new variety is less serrated and more splitting and more resistant to *Fusarium oxysporum.*

We claim:

1. The new and distinct standard carnation, substantially as herein shown and described, characterized by its large flowers of uniform bright red color, its profuse production of blooms produced recurrently in spring, midseason and fall, its rather long flower stem, and its vigorous and upright growth habit with moderately abundant foliage.

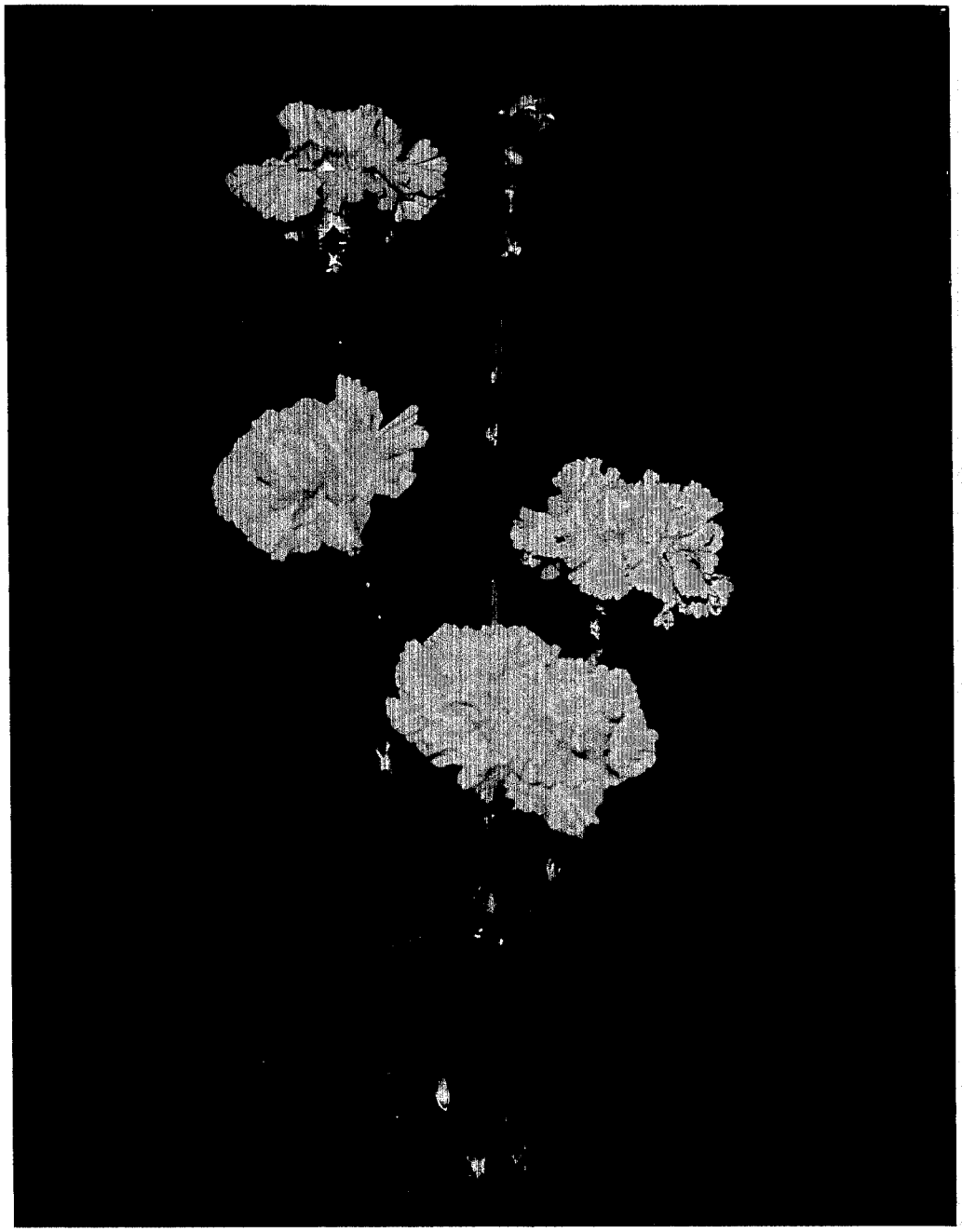

* * * * *